United States Patent [19]

Brierley et al.

[11] Patent Number: 4,786,169

[45] Date of Patent: Nov. 22, 1988

[54] OPTICAL ANALYTICAL INSTRUMENT FOR TESTING THE TRANSMISSION AND REFLECTION OF A SAMPLE

[75] Inventors: Philip R. Brierley; Doug Pfrang, both of Madison, Wis.

[73] Assignee: Nicolet Instrument Corporation, Madison, Wis.

[21] Appl. No.: 763,919

[22] Filed: Aug. 8, 1985

[51] Int. Cl.[4] ............................................. G01N 21/01
[52] U.S. Cl. .................................... 356/244; 356/73
[58] Field of Search ........................ 356/73, 244, 346; 250/343, 347, 353

[56] References Cited

U.S. PATENT DOCUMENTS

| | | | |
|---|---|---|---|
| 3,687,519 | 8/1972 | Mapes | 356/73 |
| 3,958,882 | 5/1976 | Gast | 356/73 |
| 3,977,786 | 8/1976 | Gast | 356/244 |
| 3,977,787 | 8/1976 | Fletcher et al. | 356/346 |
| 4,120,582 | 10/1978 | DeVries et al. | |
| 4,171,909 | 10/1979 | Kramer et al. | |
| 4,269,518 | 5/1981 | Rahn | |
| 4,473,295 | 9/1984 | Doyle | 356/244 |
| 4,479,058 | 10/1985 | Gast et al. | 356/244 |
| 4,506,158 | 3/1985 | Cadwallader et al. | 356/244 |
| 4,653,880 | 3/1987 | Sting et al. | |

FOREIGN PATENT DOCUMENTS

| | | |
|---|---|---|
| 2606675 | 9/1977 | Fed. Rep. of Germany . |
| 2757196 | 6/1979 | Fed. Rep. of Germany . |
| 1481477 | 4/1967 | France . |
| 2119507 | 11/1983 | United Kingdom . |
| 2136594 | 9/1984 | United Kingdom . |

OTHER PUBLICATIONS

European Search Report (3 pages).
Brochure by Nicolet Instrument Corporation entitled "Fourier Transform Infrared Spectrometer Series 20DXB/20SXB".
Brochure by Nicolet Instrument Corporation entitled "Optical Layouts and Specifications of Nicolet FT-IR Spectrometers".

Primary Examiner—Vincent P. McGraw
Assistant Examiner—S. A. Turner
Attorney, Agent, or Firm—Lathrop & Clark

[57] ABSTRACT

An analytical instrument includes an optical system having a source of incoming radiation (11) which in a transmission test is focused by a primary focusing element (15) onto a sample (16). The radiation transmitted through the sample is collimate by a focusing-collimating element (20) and directed across the beam of incoming radiation (14) before focused on a detector (12). To perform a test of the reflectance of the sample, an intercept element (28) is moved into position in the incoming beam (14) to deflect a portion (36) of the beam which is directed to the focusing-collimating element (20) and focused on the sample. The reflected radiation from the sample is collected by the focusing-collimating element (20) into a collimated beam (38) that is parallel and adjacent to the incoming beam, and which is directed in a path which passes by the intercept element (28) to be focused onto the detector (12). By selectively moving the intercept element (28) into and out of the path of the beam (14), a sample may be analyzed for both transmission and reflectance characteristics without moving the sample.

31 Claims, 4 Drawing Sheets 4,786,169

OPTICAL ANALYTICAL INSTRUMENT FOR TESTING THE TRANSMISSION AND REFLECTION OF A SAMPLE

FIELD OF THE INVENTION

This invention pertains generally to the field of optical analytical instruments as exemplified by infrared spectrometers.

BACKGROUND ART

Various types of optical analytical instruments have been developed which direct analytical radiation, e.g., infrared, to an optical system which focuses the beam of radiation on a sample. The radiation transmitted through or reflected from the sample is then directed by further optics to a detector. Such optical systems are particularly used in infrared spectrometers.

In an optical system employed in infrared spectroscopy, the radiation beam from the source is typically collimated and directed to a focusing element which focuses the beam on the sample. If the radiation transmitted through the sample is to be analyzed, another focusing element is mounted on the opposite side of the sample to collect the radiation that is passed through the sample and to collimate it. The collimated beam may then be deflected one or more times before being directed to a focusing element which focuses the beam on the detector. If, however, the reflected radiation from the sample is to be analyzed, a separate optical system is used in which the radiation reflected from the sample is collected and directed to and focused upon a detector. Such dedicated reflectance systems are relatively expensive and thus have had limited use. Additionally, to test a single sample for both transmission and reflection, the sample must be moved from one optical system to the other and the optics properly aligned, a time consuming task. Because two separate optical systems are used, it has been difficult to accurately analyze the transmission and reflection characteristics of the same sample under comparable conditions to determine the absorption of the sample.

SUMMARY OF THE INVENTION

In accordance with the present invention, an optical system is provided for an analytical instrument which allows analysis of radiation transmitted through and specularly reflected from a sample without the need to move the sample. The reflectance test is performed utilizing substantially the same optical components utilized to perform the transmission analysis and without readjustment of the positions of the optical components. Thus, the absorption of a sample may readily be measured by performing consecutive transmission and reflection tests.

The optical system receives an incoming beam of collimated radiation from a source. During a transmission test, the collimated beam is incident upon a primary focusing element, e.g., a parabolic mirror, which deflects and focuses the beam onto a sample held in a sample support. The radiation transmitted through the sample spreads out and is collected by a focusing-collimating element, e.g., another parabolic mirror, which collimates the transmitted radiation into a beam. The beam is then directed across the incoming beam to another focusing element which focuses the beam onto a detector.

For a reflectance test, the initial path of the beam through the optics to the sample is the reverse of the path of the beam during a transmission test, with the reflected radiation from the sample following the same path through the optical system to the detector. Thus, many of the same optical elements are utilized without adjustment to make the reflectance tests as are used in the transmission tests. This is accomplished by inserting an intercept element into a portion of the incoming collimated beam from the source at the position at which the incoming beam and the beam returning from the sample cross. The intercept element, e.g., a flat mirror, redirects a portion of the incoming beam backwards through the optical path to the focusing-collimating element, which focuses the beam onto the sample in the sample support. The radiation reflected from the sample is collected by the focusing-collimating element and directed back to the detector. Because the intercept element deflects only a portion of the collimated beam from the source, the incoming radiation directed to the sample and the retaining radiation reflected from the sample occupy different, generally parallel regions in space in the optical system so that they do not interfere with one another. The portion of the collimated beam not intercepted may be blocked with a radiation absorbing or deflecting element so that it does not reach the sample.

In a modified embodiment of the optical system of the present invention, it is possible to simultaneously analyze the reflection and transmission characteristics of a sample. In such modified embodiment, the collimated beam from the source is intercepted and a portion thereof deflected to the sample and the reflected radiation directed to and focused upon a detector as described above. In addition, the portion of the beam focused on the sample which is transmitted through the sample is collected by an element which provides a collimated beam which is then focused upon a second detector.

The optical elements of the system preferably comprise reflecting mirrors to maximize the energy of the radiation that reaches the detector, although appropriate refracting elements may also be utilized.

Further objects, features, and advantages of the invention will be apparent from the following detailed description when taken in conjunction with the accompanying drawings.

DESCRIPTION OF THE PREFERRED EMBODIMENT

Figure 1:
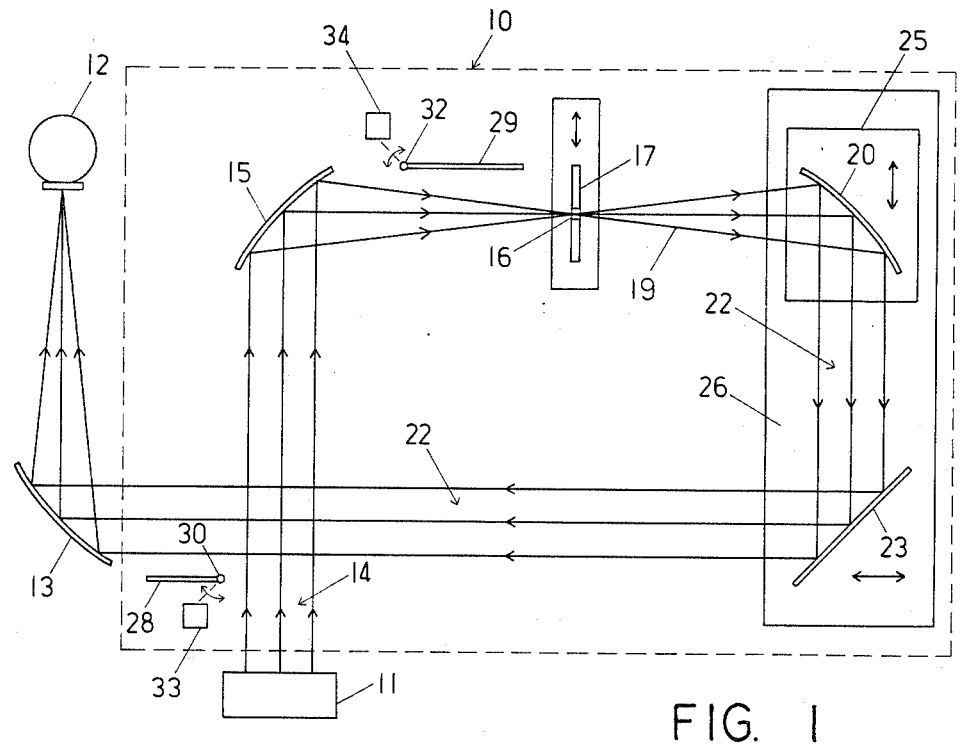
FIG. 1 is a simplified top plan view of an analytical instrument incorporating the optical system of the present invention arranged to perform a transmission test.

With reference to the drawings, an optical system incorporating the present invention is shown generally within the dashed lines labeled 10 in FIG. 1 and forms part of an analytical instrument which also includes a source 11 of collimated radiation, a detector 12, and a detector focusing element 13 which focuses the analytical radiation on the detector 12. The optical system 10 is shown in FIG. 1 in a configuration for performing a transmission test on a sample. The collimated incoming beam 14 of electromagnetic radiation from the source 11 is received within the optical system 10 on a primary focusing element 15, a parabolic mirror shown, which focuses the radiation down to a small spot on a sample 16 held within a sample support 17. The support 17 is a conventional structure which holds the sample to be analyzed in a known manner so that radiation can pass through the sample or be reflected from it from either side of the support 17. The support is also preferably capable of moving laterally—as shown by the arrows in FIG. 1—and up and down, and holds the sample for rotation about the center axis of the sample to allow precision alignment.

The radiation 19 transmitted through the sample is collected by a focusing-collimating element 20, e.g., a parabolic mirror, which collimates the radiation into a beam 22 which is directed to the detector focusing element 13 by a deflecting element 23, e.g., a flat mirror. It is also apparent that the focusing-collimating element 20 could direct the beam 22 directly at the detector focusing element 13 or that additional deflecting elements could be interposed in the optical path between the two elements if desired. The path of the returning beam 22 is arranged to cross the path of the incoming beam 14, as illustrated in FIG. 1. The focusing-collimating element 20 is mounted on a platform 25 which itself is mounted on a platform 26 to which the deflecting element 23 is mounted. The platform 26 is capable of adjustable movement, left and right in the view of FIG. 1, to allow the energy throughput of samples of various sizes to be optimized, and the platform 25 is mounted to the platform 26 for motion transverse to the allowed direction of motion of the platform 26 to allow the element 20 to be positioned to accommodate different types of samples or sampling accessories, as in the study of attenuated total reflectance (ATR). Such adjustable mountings for beam condenser optics are further described in copending application Ser. No. 472,026, filed Mar. 4, 1983, entitled Optical Analytical Instrument Beam Consenser. The elements within the dashed line labeled 10 may be maintained, if desired, in a dedicated sample compartment which can be purged with dry air or nitrogen to minimize the effects of moisture and carbon dioxide on the radiation. The focal lengths of the focusing elements 13, 15 and 20 are also preferably selected to maximize the energy throughput of the instrument.

Also included in the optical system 10 are an intercept element 28 and a blocking element 29, both of which are in their retracted positions in FIG. 1 in which neither one affects the path of radiation through the optical system 10. The intercept element 28, e.g., a flat mirror, is mounted to rotate about a pivot 30. Similarly, the blocking element 29, e.g., a sheet of infrared absorber material, is mounted to rotate about a pivot 32. For illustrative purposes, an operating element 33 is shown connected to the intercept element 28 to rotate the same about its pivot 30. The operating element 33 can be any suitable driver for rotating the element, for example, a simple linkage connected to a handle which can be turned by the user, or an automatic device such as a solenoid or a stepping motor connected to the intercept element by a linkage. Similarly, an operating element 34 of the same type is shown operatively connected to the blocking element 29 to selectively rotate the same at the user's command.

Figure 2:
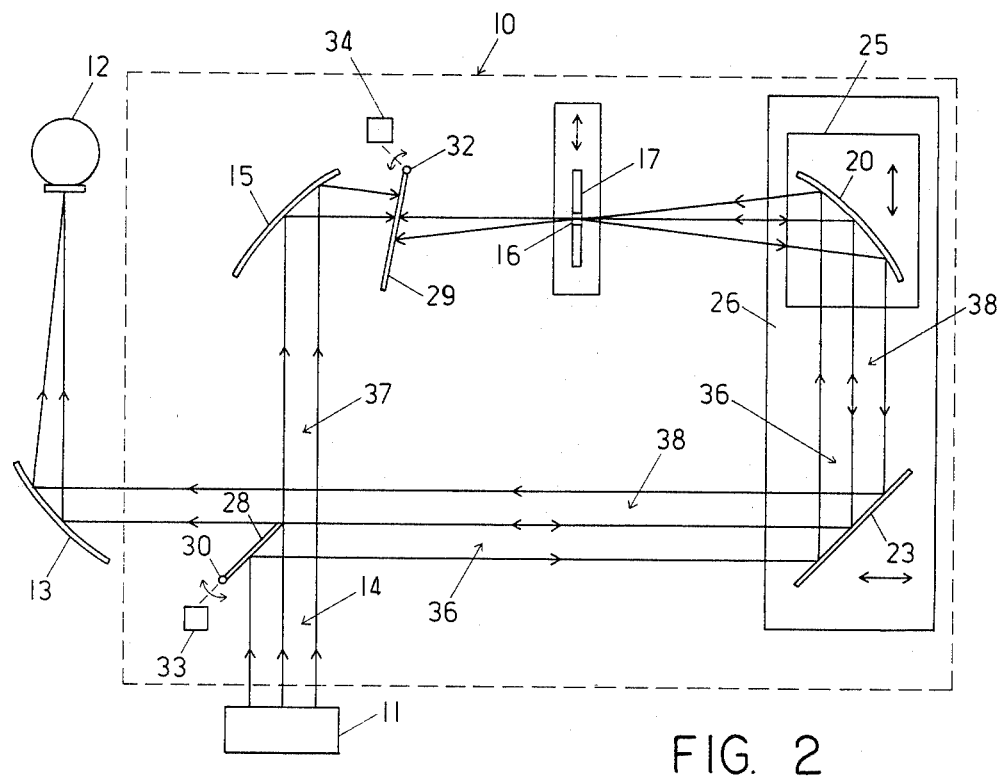
FIG. 2 is a top plan view of the analytical instrument of FIG. 1 shown arranged to perform a reflectance test.

When a reflectance test is to be performed, the operators 33 and 34 are activated to rotate the elements 28 and 29 to their operative positions shown in FIG. 2. The intercept element 28 is interposed in the path of the incoming collimated beam 14 at the position at which the incoming beam 14 and returning beam 22 cross. The element 28 preferably intercepts one-half of the incoming beam. The intercepted portion 36 of the beam is deflected toward the deflecting element 23 while the portion 37 of the beam which is not deflected proceeds to fall on the focusing element 15 which deflects the beam onto the energy absorbing surface of the blocking element 29.

The intercepted beam portion 36 is deflected by the element 23 toward the focusing-collimating element 20. Since the beam 36 follows essentially the same path as the radiation transmitted through the sample during the transmittance test, but in the opposite direction, it is focused by the element 20 onto a small spot on the surface of the sample 16. A portion of the focused radiation is transmitted through the sample and is blocked and absorbed by the blocking element 29. The radiation specularly reflected off of the sample 16 is collected by the element 20 and collimated into a beam 38 which follows essentially the same path as does the beam 22 in the transmittance test. The beam 38 is deflected by the element 23 and passes by but is not impeded by the intercept element 28. The beam 38 therefore falls upon the focusing element 13 and is focused onto the detector 12.

Figure 3:
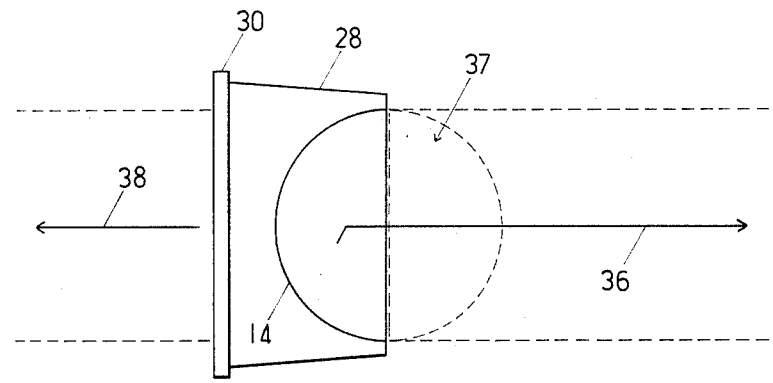
FIG. 3 is a front perspective view of the intercept element of the instrument of FIGS. 1 and 2.

A front perspective view looking toward the intercept element 28 as seen from the source 11 is shown in FIG. 3. The collimated beam of radiation 14, the position of which is illustratively shown by the line labeled 14 in FIG. 3, is partially intercepted by the intercept element 28. This portion of the beam is deflected to the right in the view of FIG. 3 and forms the beam portion 36. The nondeflected portion 37 of the beam is shown within the semicircle bounded by the dashed lines in FIG. 3. As also illustrated in FIG. 3, the returning radiation reflected from the sample forming the beam 38 passes by behind the intercept element 28 and crosses the path of the beam portion 37. The element 28 may be a flat or planar mirror formed to efficiently reflect the range of wavelengths of radiation that are utilized in the analytical instrument.

Figure 4:
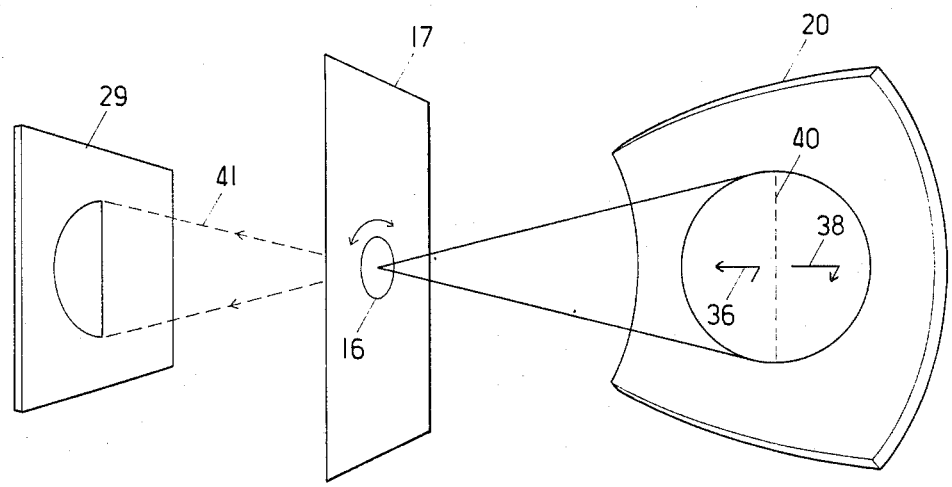
FIG. 4 is an illustrative perspective view of the focusing-collimating element, sample support, and blocking element of the instrument of FIGS. 1 and 2.

For illustrative purposes, the paths of the incident and reflected radiation are shown in FIG. 4 with respect to the focusing-collimating element 20, the sample support 17, and the blocking element 29. The beam portion 36 is, essentially, a semicircular beam which impinges upon the surface of the focusing-collimating element 20

(e.g., parabolic mirror surface) and is deflected toward and focused upon the sample 16. The reflected radiation from the sample 16 occupies a complementary semicircular region in space to the right-hand side of the dashed line labeled 40 in FIG. 4 and is collimated by the element 20 into the beam 38 which essentially occupies the semicircular region adjacent and parallel to the semicircular beam 36. The radiation which is transmitted through the sample 16, illustrated by the diverging dashed lines labeled 41 in FIG. 4, falls on the surface of the blocking element 29 and is absorbed.

Figure 5:
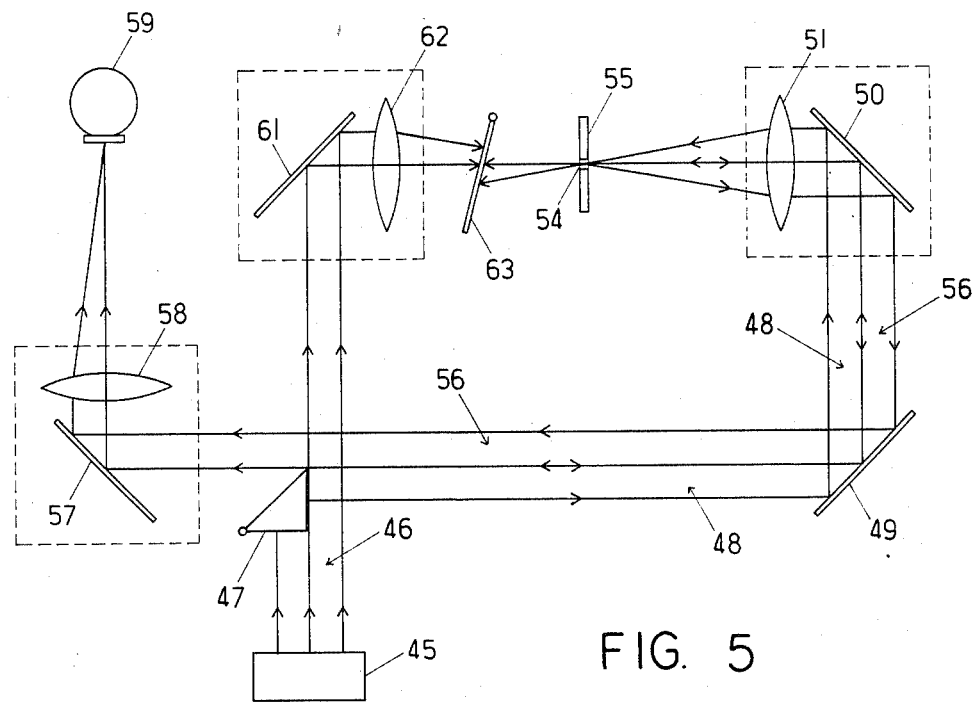
FIG. 5 is a modified embodiment of an instrument in accordance with the invention utilizing refracting elements for focusing and collimating the analyzing radiation.

Reflecting mirrors are preferred for the focusing elements 13, 15, and 20 because such elements scatter and attenuate the analytical radiation less than refracting elements. However, it is apparent that refracting elements may also be utilized where appropriate, and an example of a system using refracting elements is illustrated in FIG. 5. The source 45 shown therein produces a collimated beam of incoming analytical radiation 46, a portion of which is intercepted by a prism intercept element 47 and deflected in a beam 48 toward a deflecting element 49. The prism 47 is mounted to be selectively moved into and out of the beam 46 at the command of the user. The beam 48 is deflected again by another deflecting mirror 50 and focused by a lens 51, the elements 50 and 51 together serving the same function as the focusing-collimating parabolic mirror 20. The deflected portion 52 of the beam which is focused on a sample 54 held in a support 55 is partially reflected back to the focusing-collimating lens 51 which collimates the radiation into a beam 56. This beam is deflected by the flat mirror 50 back toward the deflecting mirror 49 and thence to a further deflecting mirror 57 and focusing lens 58 which focuses the beam on a detector 59. The portion of the beam that is not intercepted by the prism 47 proceeds on to a deflecting element 61 and a lens 62 which together perform the function of the primary focusing element 15. The portion of the beam deflected and focused by the elements 61 and 62 is absorbed by a blocking element 63 having energy absorbing surfaces which is interposed in the path of the beam.

For tests of the transmission of radiation through the sample 54, the intercept element prism 47 and the blocking element 63 are flipped out of the way of the beams and the full collimated beam 46 is focused on the sample 54 for analysis of the transmission characteristics of the sample in the manner described above.

Figure 6:
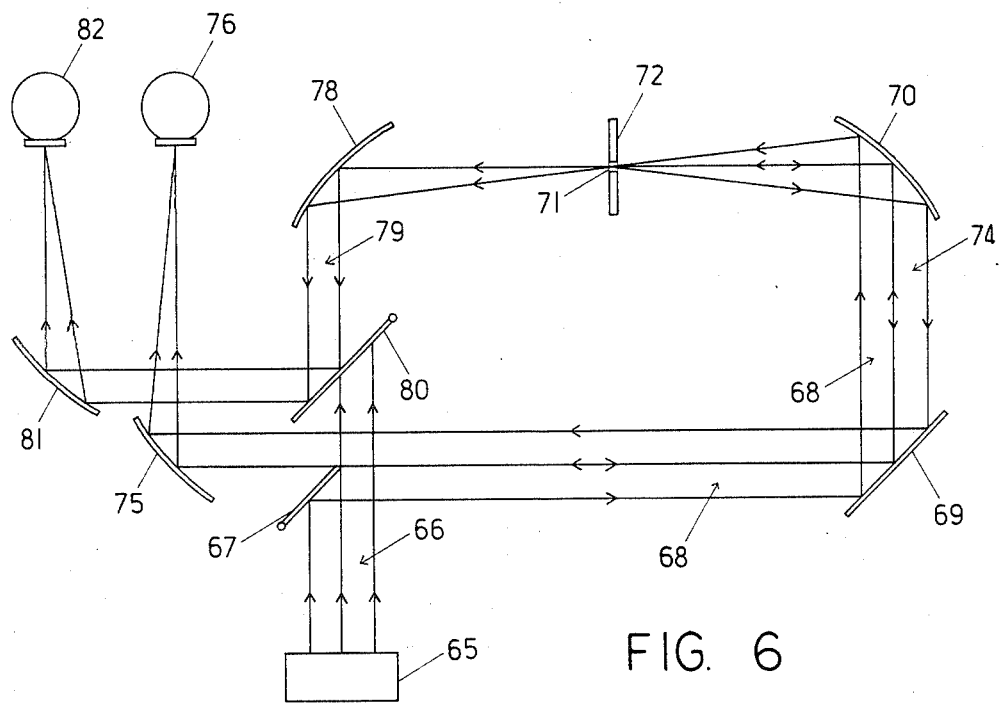
FIG. 6 is a top plan view of another modified embodiment of the invention in which a second detector is provided to allow simultaneous determination of the radiation reflected from and transmitted through a sample.

A modified embodiment which allows simultaneous analysis of the transmission and reflection characteristics of a sample is illustrated in FIG. 6. Again, a source 65 of analytical radiation produces a collimated incoming beam 66, a portion of which is intercepted and deflected by an intercept element 67. The deflected portion 68 of the beam deflects off a deflecting element 69, e.g., a flat mirror, is deflected and focused off a focusing-collimating element 70, e.g., a parabolic mirror, and reaches a sample 71 held in a support 72. Some of the analytical radiation is reflected off of the sample 71 and back toward the element 70, where it is collected and formed into a collimated beam 74 which deflects off of the element 69 past the intercept element 67, crossing the path of the non-intercepted portion of the incoming beam 66, and falls on a first detector focusing mirror element 75 which focuses the beam onto a first detector 76.

Some of the analytical radiation striking the sample 71 is transmitted through the sample and diverges toward a primary focusing parabolic mirror 78 which collects the radiation, focuses it into a collimated beam 79 and directs the beam toward the mirror face of a blocking element 80, which further deflects the beam to a second detector focusing mirror 81 which focuses it on a second detector 82. The portion of the beam 66 which is not intercepted by the intercept element mirror 67 strikes the back side of the element 80 and is blocked thereby, e.g., by being absorbed at the energy absorbing face of this element. The optical analytical instrument of FIG. 6 is also configured to allow the full beam to be focused upon the sample 71 for a transmission test by rotating the elements 67 and 80 out of the path of the beams which they intercept when in the configuration of FIG. 6. It should be apparent from an examination of the system of FIG. 6 that the blocking element 80 performs essentially the same function as the blocking elements 29 and 63 in that it prevents the radiation from the portion of the beam 66 which is not intercepted, and the portion of the radiation that is transmitted through the sample, from interfering with the measurement of the radiation which is reflected from the sample.

Figure 7:
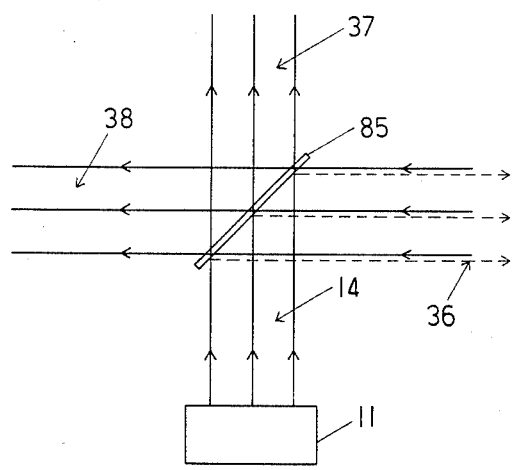
FIG. 7 is a simplified top plan view of an alternative intercept element.
Figure 8:
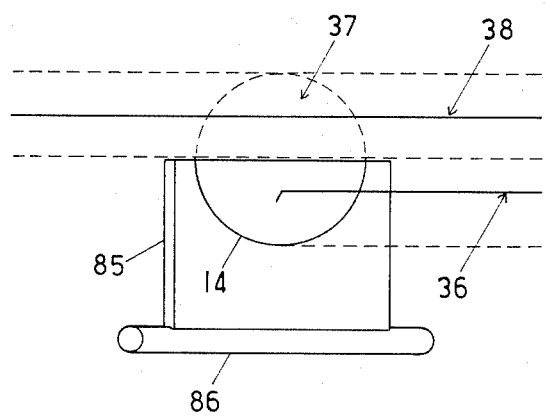
FIG. 8 is a front perspective view of the intercept element of FIG. 7.

A further modified embodiment for the intercept element, i.e., the element 28, 47, or 67, is illustrated in FIG. 7 at 85. The intercept element 85 comprises a flat mirror which rotates about a pivot 86 and may be driven into and out of its intercept position in the manner described above. However, the intercept element 85 is mounted with its pivot 86 below the position of the incoming beam of radiation 14 from the source 11, specific reference being had to the views of FIGS. 1 and 2 wherein the intercept element 85 is substituted for the intercept element 28, all other components of the optical system 10 being the same. As best shown with respect to the view of FIG. 8, a view looking toward the intercept element 85 along the path of the collimated beam 14, the intercept element 85 deflects the lower half of the beam 14 into the outgoing beam portion 36. The upper portion 37 of the beam 14 which passes over the top of the intercept element 85 reaches the blocking element 29 and is absorbed. The beam portion 36 is deflected and focused by the elements 23 and 20 as before onto the sample 16, and the reflected radiation from the sample, which now occupies the space complementary to the beam half portion 36, is collimated by the element 20 into the beam 38 which is deflected by the deflecting mirror 23 and now passes unimpeded over the top of the mirror 85 toward the focusing element 13 and the detector 12. One advantage of the configuration for a deflecting element 85 which intercepts the bottom half portion of the beam 14 is that the beam portion 36 and the beam portion 38 never intersect one another in their paths to and from the sample.

The present invention is particularly useful in infrared analysis systems, such as are found in Fourier transform infrared spectrometers. A variety of infrared sources are commercially available and can be chosen to cover the wavelengths desired. Common detectors for infrared include deuterated triglycerine sulfate (DTGS) pyroelectric bolometers and mercury cadmium telluride (MCT) detectors.

It is apparent that there may be many modifications of the specific components of the invention without departing from the scope and spirit of the invention. As specific examples, the intercept elements 28, 47, 67, and 85 may be mounted by any appropriate mechanical means for moving them into and out of the path of the incoming beam 14, such as by being mounted on slides for movement laterally into and out of the beam, or by being mounted about a rotary axis which is perpendicular to the plane of the elements so that they may be selectively moved into and out of their intercept positions by rotation about such an axis. It is also apparent that the position of the elements illustrated above may be rearranged and configurations employed which utilize more or fewer elements but still direct the beams of radiation to and from the sample such that the radiation returning from the sample crosses the path of the incoming beam.

It is further understood that the invention is not confined to the particular structures and techniques described herein as exemplary, but embraces such modified forms thereof as come within the scope of the following claims.

What is claimed is:

1. In an analytical instrument designed for testing the transmission and reflection of a sample, the instrument being of the type having a source providing a collimated beam of analytical radiation, a support for supporting the sample to be analyzed, a detector for detecting the analytical radiation, and means for focusing analytical radiation on the detector, the improved beam directing system comprising:
   primary focusing means, mounted in position to receive the incoming beam from the source, for focusing the beam so received on a sample held in the sample support means,
   focusing-collimating means for focusing a collimated beam of analytical radiation which is incident thereon onto a sample supported in the sample support and for receiving analytical radiation reflected from the sample and collimating it into a beam which is directed to the means for focusing analytical radiation onto the detector, and
   intercept means for selectively redirecting a portion of the collimated beam of analytical radiation from the source into the focusing-collimating means such that the redirected portion of the beam will be focused on the sample without moving the sample and the radiation reflected from the sample will be collimated by the focusing-collimating means and directed back past the intercept means to the means for focusing analytical radiation on the detector, wherein the intercept means is activated to test the reflection of the sample, and such that substantially the same focusing-collimating means is used in testing both the reflection and transmission of the sample.

2. The instrument of claim 1 including primary focusing means, in the path of the beam from the source, for focusing radiation incident thereon onto the sample held in the support such that radiation transmitted through the sample is collected and collimated by the focusing-collimating means and directed to the means for focusing analytical radiation on the detector on a path which crosses the path of the incoming beam from the source, and wherein the intercept means is selectively insertable into the path of the beam from the source at the position where it is crossed by the beam returning from the sample such that, when the intercept means is out of the path, the beam of radiation is focused by the primary focusing means onto the sample and is transmitted therethrough to the focusing-collimating means which collimates the beam and directs it to the means for focusing the beam onto the detector.

3. The instrument of claim 2 including blocking means selectively interposable into the path of radiation from the primary focusing means to the sample for blocking the radiation from the primary focusing means from reaching the sample when the intercept means is interposed in the path of the beam from the source.

4. The instrument of claim 1 wherein the focusing-collimating means comprises a parabolic mirror and the intercept means comprises a flat deflecting mirror.

5. The instrument of claim 3 wherein the primary focusing means and the focusing-collimating means comprise parabolic mirrors, and the intercept means comprises a flat deflecting mirror mounted to be selectively interposed into the path of the radiation from the source so that, when so interposed, it deflects a portion of the beam to the focusing-collimating means.

6. The instrument of claim 5 wherein the deflecting mirror of the intercept means is mounted to a pivot to be rotated from a position in which the mirror is outside of the path of the beam from the source to a position in which the mirror intercepts substantially one-half of the beam from the source.

7. The instrument of claim 1 wherein the intercept means intercepts substantially one-half of the collimated beam from the source and deflects it to the focusing-collimating means, and wherein the portion of the beam intercepted by the intercept means and directed to the sample and the beam of radiation reflected from the sample to the focusing-collimating means and collimated by it are substantially parallel and adjacent to each other.

8. The instrument of claim 1 wherein the focusing-collimating means includes a parabolic mirror mounted to collect radiation from the sample and collimate it and a flat deflecting mirror mounted to deflect the beam from the parabolic mirror, the parabolic mirror and deflecting mirror mounted together for motion in a first direction toward and away from the sample support, and wherein the parabolic mirror is mounted for motion toward and away from the deflecting mirror in a second direction transverse to the first direction.

9. The instrument of claim 2 wherein the instrument has a second detector and second means for focusing analytical radiation on the second detector, and including means for selectively blocking the portion of the incoming beam which is not intercepted from reaching the sample and for selectively directing radiation transmitted through the sample and collimated by the primary focusing means to the second means for focusing to focus the radiation on the second detector, whereby the reflectance characteristics of the sample can be detected by the first detector and the transmission characteristics of the sample can be simultaneously detected by the second detector.

10. An analytical instrument which uses analyzing radiation to test the transmission and reflection of a sample comprising:
   (a) a source which provides a collimated beam of analytical radiation;
   (b) detector means for detecting the analytical radiation;
   (c) support means for supporting the sample to be analyzed;
   (d) primary focusing means, mounted in position to receive the incoming beam from the source, for focusing the beam so received on a sample held in the sample support means;

(e) detector focusing means for focusing radiation received onto the detector;

(f) focusing-collimating means for collimating analytical radiation received from the sample into a beam and directing it to the detector focusing means on a path which crosses the path of the incoming beam from the source and for focusing collimated radiation received on the sample; and (g) intercept means selectively interposable into the incoming beam from the source at the position at which it crosses the beam from the focusing-collimating means for, when interposed into the incoming beam, directing a portion of the incoming beam to the focusing-collimating means such that the portion of the beam is focused on the sample in the support and the radiation reflected off of the sample back to the focusing-collimating means is collimated into a beam directed to the detector focusing means and is focused on the detector means, wherein the intercept means is activated to test the reflection of the sample so that substantially the same focusing-collimating means are used in testing both the reflection and transmission of the sample.

11. The instrument of claim 10 including blocking means selectively interposable into the path of radiation from the primary focusing means to the sample for blocking the radiation from the primary focusing means from reaching the sample when the intercept means is interposed in the path of the beam from the source.

12. The instrument of claim 10 wherein the focusing-collimating means comprises a parabolic mirror and the intercept means comprises a flat deflecting mirror.

13. The instrument of claim 11 wherein the primary focusing means and the focusing-collimating means comprise parabolic mirrors, and the intercept means comprises a flat deflecting mirror mounted to be selectively interposed into the path of the radiation from the source so that, when so interposed, it deflects a portion of the beam to the focusing-collimating means.

14. The instrument of claim 13 wherein the deflecting mirror of the intercept means is mounted to a pivot to be rotated from a position in which the mirror is outside of the path of the beam from the source to a position in which the mirror intercepts substantially one-half of the beam from the source.

15. The instrument of claim 10 wherein the intercept means intercepts substantially one-half of the collimated beam from the source and deflects it to the focusing-collimating means, and wherein the portion of the beam intercepted by the intercept means and directed to the sample and the beam of radiation reflected from the source to the focusing-collimating means and collimated by it are substantially parallel and adjacent to each other.

16. The instrument of claim 10 wherein the focusing-collimating means includes a parabolic mirror mounted to collect radiation from the sample and collimate it and a flat deflecting mirror mounted to deflect the beam from the parabolic mirror, the parabolic mirror and deflecting mirror mounted together for motion in a first direction toward and away from the sample support, and wherein the parabolic mirror is mounted for motion toward and away from the deflecting mirror in a second direction transverse to the first direction.

17. The instrument of claim 10 including a second detector and second means for focusing analytical radiation on the second detector, and including means for selectively blocking the portion of the incoming beam which is not intercepted from reaching the sample and for selectively directing radiation transmitted through the sample and collimated by the primary focusing means to the second means for focusing to focus the radiation on the second detector, whereby the reflectance characteristics of the sample can be detected by the first detector and the transmission characteristics of the sample can be simultaneously detected by the second detector.

18. The instrument of claim 17 wherein the means for selectively blocking comprises a blocking element having a flat deflecting mirror face which deflects the beam from the primary focusing means to the second means for focusing and a radiation absorbing face which blocks and absorbs the portion of the incoming beam not intercepted by the intercept means.

19. The instrument of claim 10 wherein the primary focusing means and the focusing-collimating means each comprise a refracting lens and a deflecting mirror.

20. An optical system for an analytical instrument designed for testing the transmission and reflection of a sample, the optical system having a source of a collimated beam of radiation, a detector for detecting the radiation, and a support which supports the sample to be analyzed, comprising:

(a) optical elements arranged to receive the incoming beam of radiation from the source, focus the radiation on the sample, collimate the radiation transmitted through the sample into a beam and direct the beam to the detector in a path which crosses the path of the incoming beam from the source; and (b) intercept means selectively interposable into the incoming beam from the source at the position at which it crosses the beam directed to the detector for, when interposed into the beam, directing a portion of the incoming beam backwardly along the path of radiation through the optical elements so that the beam portion is focused on the sample without moving the sample and the radiation reflected off of the sample is collimated in a beam directed to the detector back past the intercept means, wherein the intercept means is activated to test the reflection of the sample, so that the optical elements which collimate the radiation transmitted through the sample into the beam and direct the beam to the detector are used to test both the transmission and reflection of the sample.

21. The system of claim 20 including blocking means for blocking the portion of the incoming beam from the source which is not intercepted by the intercept means from reaching the sample when the intercept means is interposed in the path of the beam from the source.

22. The system of claim 21 wherein the optical elements which focus the incoming beam of radiation on the sample and collimate the radiation from the sample comprise parabolic mirrors and, the intercept means comprises a flat deflecting mirror.

23. The system of claim 20 wherein the intercept means comprises a flat deflecting mirror mounted to a pivot to be rotated from a position in which the mirror is outside of the path of the beam from the source to a position in which the mirror intercepts substantially one-half of the beam from the source.

24. A method of analyzing a sample with analytical radiation comprising the steps of:

(a) providing a collimated beam of analytical radiation;

(b) deflecting a portion of the collimated beam out of the path of the beam;

(c) focusing the deflected portion of the beam onto a sample; and (d) collimating the radiation reflected from the sample into a beam and directing it back along a path parallel to the path of the incoming deflected beam portion.

25. The method of claim 24 including the step of focusing the beam of reflected radiation onto a detector for such radiation.

26. The method of claim 25 including the further steps of collimating the analytical radiation passed through the sample into a beam and focusing the beam of transmitted radiation onto another detector to simultaneously detect the analytical radiation transmitted through the sample and the analytical radiation reflected from the sample.

27. The method of claim 25 wherein the analytical radiation in the step of providing a beam of analytical radiation is infrared.

28. An optical system for analytical instrument designed for testing the transmission and reflection of a sample, the optical system having a source of a collimated beam of radiation, a detector for detecting the radiation, and a support which supports the sample to be analyzed, comprising:

(a) optical elements arranged to receive the incoming beam of radiation from the source, focus the radiation on the sample, collimate the radiation transmitted through the sample into a beam and direct the beam to the detector; and (b) intercept means selectively interposable into the incoming beam from the source for deflecting the radiation passing through the optical elements such that radiation reflected from the sample without moving the sample is directed backwardly through the optical elements and focused on the detector, wherein the intercept means is activated to test the reflection of the sample so that the optical elements which collimate the radiation transmitted through the sample into the beam and direct the beam to the detector are used to test both the transmission and reflection of the sample.

29. The system of claim 28 wherein the optical elements which focus the incoming beam of radiation on the sample and collimate the radiation from the sample comprise parabolic mirrors and the intercept means comprises a flat deflecting mirror.

30. The system of claim 28 wherein the intercept means comprises a flat deflecting mirror mounted to a pivot to be rotated from a position in which the mirror is outside of the path of the beam from the source to a position in which the mirror intercepts substantially one-half of the beam from the source.

31. A method of analyzing a sample with analytical radiation in an optical system which has a source of a collimated beam of radiation, a detector for detecting the radiation, a support which supports the sample to be analyzed, optical elements arranged to receive the incoming beam of radiation from the source, focus the radiation on the sample, collimate the radiation transmitted through the sample into a beam and direct the beam to the detector, comprising the steps of:

(a) selectively redirecting a portion of the beam from the source such that the redirected beam of analytical radiation is incident on the sample and such that the redirected beam and a beam of analytical radiation reflected from the sample follow parallel paths to and from the sample through the optical elements which focus the radiation on the sample; and (b) directing the radiation reflected from the sample back to the detector.

* * * * *